United States Patent
Inoue et al.

(10) Patent No.: US 7,109,242 B2
(45) Date of Patent: Sep. 19, 2006

(54) CARBOXYLIC COMPOUND AND MEDICINE COMPRISING THE SAME

(75) Inventors: Keisuke Inoue, Tokyo (JP); Tsutomu Toma, Tokyo (JP); Takahiro Kitamura, Tokyo (JP); Yukiyoshi Yamazaki, Tokyo (JP); Tetsuya Ishikawa, Saitama (JP)

(73) Assignee: Kowa Company, Ltd., Aichi (JP)

( * ) Notice: Subject to any disclaimer, the term of this patent is extended or adjusted under 35 U.S.C. 154(b) by 65 days.

(21) Appl. No.: 10/849,778

(22) Filed: May 21, 2004

(65) Prior Publication Data

US 2005/0009909 A1    Jan. 13, 2005

Related U.S. Application Data

(60) Provisional application No. 60/472,737, filed on May 23, 2003.

(30) Foreign Application Priority Data

May 30, 2003    (JP) ............................. 2003-154372

(51) Int. Cl.
*A01N 37/00* (2006.01)
(52) U.S. Cl. .................. 514/558; 514/557; 514/559; 514/866; 554/215
(58) Field of Classification Search ............... 514/558, 514/557, 559, 866; 554/215
See application file for complete search history.

(56) References Cited

U.S. PATENT DOCUMENTS 5,968,982 A * 10/1999 Voss et al. ................. 514/558

FOREIGN PATENT DOCUMENTS

| JP | 5-952 | 1/1993 |
| JP | 10-510515 | 10/1998 |

OTHER PUBLICATIONS

English Language Abstract of JP 5-952.

Expert Opinion on Investigational Drugs, "*Insulin Sensitiser Drugs*," vol. 9, No. 6, pp. 1347-1361, 2000.
European Journal of Medicinal Chemistry, "*ω-Substituted Alkyl Carboxylic Acids As Antidiabetic and Lipid-Lowering Agents*," vol. 33, pp. 775-787, 1998.
Metabolism, "*BM 17.0744: A Structurally New Antidiabetic Compound With Insulin-Sensitizing and Lipid- Lowering Activity*," vol. 48, No. 1, pp. 34-40, Jan. 1999.
Journal of Medicinal Chemistry, "*The Effect of 1,3-Diaryl-[1H]-pyrazole-4-acetamides on Glucose Utilization in ob/ob Mice*," vol. 44, pp. 2601-2611, Jul. 6, 2001.
Journal of Clinical Investigation, "*Glucose Transporter Levels in Spontaneously Obese (db/db) Insulin-resistant Mice*," vol. 85, pp. 962-967, Mar. 1990.
Arznimittel-Forschung, "*Effects of Pioglitazone on Glucose and Lipid Metabolism in Normal and Insulin Resistant Animals*," vol. 40, pp. 156-162, 1990.
Archives of Toxicology, "*Species Differences in Induction of Hepatic Enzymes by BM 17.0744, An Activator of Peroxisome Proliferator-Activated Receptor Alpha (PPARα)*," vol. 73, pp. 440-450, 1999.

* cited by examiner

*Primary Examiner*—Johann Richter
*Assistant Examiner*—Chukwuma Nwaonicha
(74) *Attorney, Agent, or Firm*—Greenblum & Bernstein, P.L.C.

(57) ABSTRACT

A compound represented by the following general formula (1), a salt thereof, or an ester thereof:

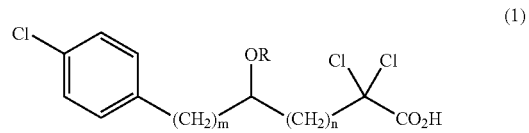

(1)

wherein m represents an integer of 0 to 4, n represents an integer of 5 to 9, and R represents hydrogen atom or a protective group of hydroxyl group, which has reducing actions of blood glucose, plasma insulin, and triglyceride, and is useful for preventive and/or therapeutic treatment of diabetes, complications of diabetes, hyperlipemia and others.

8 Claims, No Drawings

CARBOXYLIC COMPOUND AND MEDICINE COMPRISING THE SAME

This application claims the benefit of U.S. Provisional Application No. 60/472,737, filed on May 23, 2003, and also claims priority of Japanese Patent Application No. 2003-154372, filed on May 30, 2003, the disclosures of both being incorporated herein by reference in their entireties.

TECHNICAL FIELD

The present invention relates to a carboxylic compound which exerts potent hypoglycemic action, plasma insulin decreasing action, and triglyceride decreasing action, and enables preventive and/or therapeutic treatment of diseases such as diabetes, complications of diabetes, hyperlipemia, and atherosclerosis, without causing weight gain or obesity. The present invention also relates to a medicine comprising the compound.

BACKGROUND ART

Diabetes, which is a metabolic disorder caused by plural factors, is roughly classified into Type I diabetes caused by failure of insulin secretion and Type II diabetes resulting from decline of insulin sensitivity in peripheral tissues. A rapid increase of Type II diabetes has been recognized in recent years, attributable to environmental factors such as obesity and hyperphagia as background factors. Diabetes prevalence rate in the world is estimated to be 5%.

Insulin and sulfonylurea agents are frequently used for medicinal treatments of diabetes. However, insulin and sulfonylurea agents induce hypoglycemia as a side effect and sulfonylurea agents also induce secondary pancreatic failure because of exhaustion of pancreas. Biguanide agents improve the insulin sensitivity and slightly normalize hyperglycemia, however, the agents have possibility to induce lactic acidosis. A thiazolidinedione type therapeutic medicine for diabetes, which has been recently developed, has an improving effect on insulin resistance in periphery (Expert Opinion on Investigational Drugs, 9, pp1347–1361, 2000), and is considered to achieve suitable blood glucose control without causing hypoglycemia. However, the medicine is reported to have side effects such as serious hepatic disorder. Therefore, a non-thiazolidinedione type medicine for improving insulin resistance is desired.

As a non-thiazolidinedione type compound, 2,2-dichloroalkanecarboxylic acid compound is known to lower a blood glucose level in a diabetes-model animal, and also exhibit decreasing actions of plasma insulin and plasma triglycerides (European Journal of Medicinal Chemistry, 33, pp775–787, 1998). Hyperinsulinemia suggests the presence of insulin resistance, and hyperlipemia, as a dysfunction of lipid metabolism with diabetes, is considered to be a risk factor of atherosclerosis. Therefore, improvements of the above symptoms are important for preventive and/or therapeutic treatment of diabetes and complications of diabetes.

For example, the following Compound A exert antidiabetes actions in various animal models (Compound 3e described in Eur. J. Med. Chem., 33, pp.775–787, 1998; Metabolism, 48, pp 34–40, 1999), and effectiveness thereof is considered to be superior to that of thiazolidinedione type compounds. Compound A has no PPAR γ activating action which is the mode of action of thiazolidinedione type compounds. Therefore, Compound A has an apparently different action from that of thiazolidinedione type compounds, and is expected to achieve reduction of side effects.

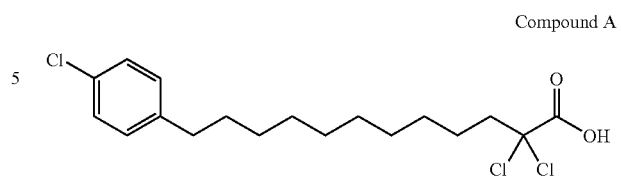

Compound A

DISCLOSURE OF THE INVENTION

In order to achieve effective treatment of diabetes and complications of diabetes, a compound is desired which has higher activity or has equal or higher activity at a lower dose to easily control a blood glucose level and to avoid drug interactions under combination with other agents, as well as to reduce or eliminate side effects.

From the forgoing point of view, a compound which is more potent than Compound A or has the same level of activity at a lower dose as compared with Compound A is expected to be useful for preventive and/or therapeutic treatment of diabetes and complications of diabetes, and moreover, hyperlipemia and atherosclerosis.

The inventors of the present invention made researches to find a more active compound. As a result, the inventors found that a carboxylic compound represented by the following general formula (1) has a potent hypoglycemic action and is useful as a medicine for preventive and/or therapeutic treatment of diabetes, complications of diabetes, hyperlipemia, atherosclerosis and others, without causing weight gain or obesity. The present invention was achieved on the basis of the above findings.

The present invention thus provides a compound represented by the following general formula (1):

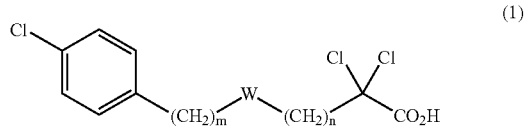

(1)

[wherein m represents an integer of 0 to 4, n represents an integer of 5 to 9, and W represents —CH(OR)— (wherein R represents hydrogen atom or a protective group of hydroxyl group) or —C(=O)—], a salt thereof, or an ester thereof.

The present invention also provides a medicine which comprises as an active ingredient a substance selected from the group consisting of a compound represented by the aforementioned general formula (1) [wherein m represents an integer of 0 to 4, n represents an integer of 5 to 9, and W represents —CH(OR)— (wherein R represents hydrogen atom or a protective group of hydroxyl group) or —C(=O)—], a physiologically acceptable salt thereof, and a physiologically acceptable ester thereof.

The aforementioned medicine can be used as a medicine for preventive and/or therapeutic treatment of a disease selected from the group consisting of hyperlipemia, atherosclerosis, diabetes, complications of diabetes, inflammation, and cardiopathy. The medicine is preferably provided as a pharmaceutical composition comprising the aforementioned substance as an active ingredient and a pharmaceutically acceptable carrier.

From another aspect, the present invention provides a use of a substance selected from the group consisting of a compound represented by the aforementioned general formula (1) [wherein m represents an integer of 0 to 4, n represents an integer of 5 to 9, and W represents —CH(OR)— (wherein R represents hydrogen atom or a protective group of hydroxyl group) or —C(═O)—], a physiologically acceptable salt thereof, and a physiologically acceptable ester thereof for the manufacture of the aforementioned medicine, and a method for preventive and/or therapeutic treatment of a disease selected from the group consisting of hyperlipemia, atherosclerosis, diabetes, complications of diabetes, inflammation, and cardiopathy which comprises the step of administering to a mammal including human an effective amount for preventive and/or therapeutic treatment of a substance selected from the group consisting of a compound represented by the aforementioned general formula (1) [wherein m represents an integer of 0 to 4, n represents an integer of 5 to 9, and W represents —CH(OR)— (wherein R represents hydrogen atom or a protective group of hydroxyl group) or —C(═O)—], a physiologically acceptable salt thereof, and a physiologically acceptable ester thereof.

BEST MODE FOR CARRYING OUT THE INVENTION

As the salt of the compound represented by the general formula (1), examples include salts of alkali metals such as sodium salt and potassium salt; salts of alkaline earth metals such as calcium salt and magnesium salt; organic base salts such as ammonium salt and trialkylamine salt; mineral acid salts such as hydrochloride and sulfate; organic acid salts such as acetate. Among these examples, physiologically acceptable salts are preferred.

The physiologically acceptable ester of the compound represented by the general formula (1) is an ester formed from the carboxyl group of the compound represented by the general formula (1), and preferred to be an ester that increase an absorption rate from intestinal canal in oral administration and is susceptible to hydrolysis after being absorbed in vivo. Examples include an alkyl ester (the alkyl group may be linear, branched, cyclic, or combinations thereof, for example the alkyl group has 1 to 20 carbon atoms, the alkyl group may contain a hetero atom such as oxygen atom and nitrogen atom on the alkyl chain and/or one or more unsaturated bond, and may have one or more optional substituents on the alkyl chain) and an aryl ester. More specifically, examples include ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester. However, the esters are not limited to these examples. Further, the physiologically acceptable amides of the compound represented by the general formula (1) may be used. An example includes methyl amide.

In the general formula (1), W represents —CH(OR)— (wherein R represents hydrogen atom or a protective group of hydroxyl group) or —C(═O)—. As a protective group of hydroxy group represented by R, a protective group which is synthetically useful (for such a protective group, "Protective Groups in Organic Synthesis," edited by P. G. M. Wuts and T. W. Greene, the 3rd edition, John Wiley & Sons, Inc. (1999) can be referred to), and further a protective group may be used which increase absorption rate of the protected compound from intestinal canal and is susceptible to deprotection in vivo to give the compound wherein R is hydrogen atom. The compound which has a protective group of the latter class is useful when the compound is used as a prodrug depending on variety of purposes. As the protective group, examples include acetyl group, palmitoyl group, propanoyl group, pivaloyl group, succinyl group, fumaryl group, alanyl group, and dimethylaminomethylcarbonyl group, however the protective group is not limited to these examples.

In the general formula (1), symbol m represents an integer of 0 to 4, symbol n represents an integer of 5 to 9, and m+n is preferable in a range of 8 to 10, more preferably 9. Symbol m is preferably an integer of 1 to 3, more preferably 1 or 2. Symbol n is preferably an integer of 6 to 9, more preferably 7 or 8.

The compound represented by general formula (1), a salt thereof, or an ester thereof may exist as a solvate which includes typically a hydrate, and any solvate falls within the scope of the present invention. Further, the compound represented by general formula (1) has one asymmetric carbon when R is hydrogen atom, and the compound of the present invention (hereinafter when "the compound of the present invention" is referred to, the term encompasses the compound represented by general formula (1) and an ester thereof) may have another one or more asymmetric carbons depending on the type of R or the ester. Stereoisomers in a pure form such as optical isomer and diastereoisomers based on one or more asymmetric carbons and any mixtures of stereoisomers such as racemates fall within the scope of the present invention.

Among the compounds of the present invention, preferable examples include 2,2-dichloro-12-(4-chlorophenyl)-10-hydroxydodecanoic acid, 2,2-dichloro-12-(4-chlorophenyl)-11-hydroxydodecanoic acid and a physiologically acceptable salt thereof, and a physiologically acceptable ester thereof.

The compound of the present invention can be prepared, for example, by the method described in the following preparation route 1 or 4. The compound of the present invention wherein m is 0 can also be prepared by the method described in the preparation route 2. Further, the compound of the present invention wherein m is 1 can also be prepared by the method described in the preparation route 3. (In the following scheme, each of m and n represents the same meaning as that mentioned above, $R^1$ represents a protective group of hydroxy group, $R^2$ represents an alkyl group, an aryl group, or allyl group, and each of X and Y represents a halogen atom.)

<Preparation Route 1>

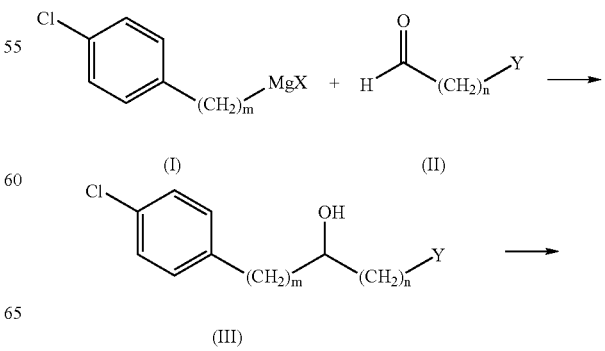

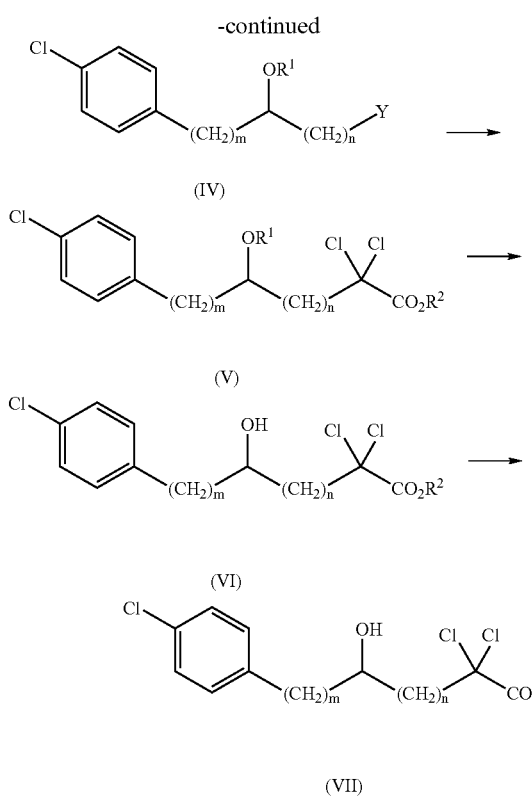

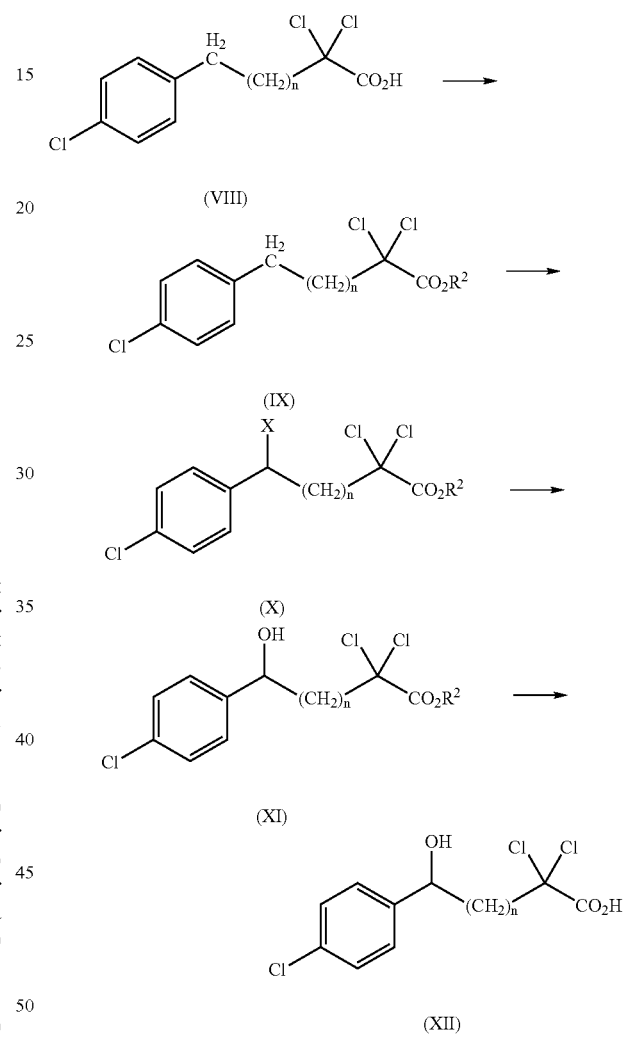

Step 5

Compound (VI) is dissolved in a solvent such as methanol, ethanol, THF, dioxane, or 1,2-dimethoxyethane. The solution is added with a base such as lithium hydroxide, sodium hydroxide, or potassium hydroxide, stirred under cooling or under heating for from one hour to 24 hours, and added with an acid such as hydrochloric acid so as to be acidic. The desired compound can thus be prepared.

<Preparation Route 2>

Step 1:

Aldehyde compound (II) is dissolved in an inert solvent such as tetrahydrofuran (THF), dioxane, ether, or dimethoxyethane. The solution is added with an inert solvent solution of Grignard reagent (I) prepared from a corresponding halide under atmosphere of an inert gas and stirred under cooling or at room temperature for 30 minutes to several hours. Compound (III) can thus be prepared.

Step 2:

This is to protect the hydroxy group of Compound (III) with a suitable protective group such as acetyl group or methoxymethyl group. As to type of the protective group and condition for introducing the protective group, for example, "Protective Groups in Organic Synthesis," edited by P. G. M. Wuts and T. W. Greene, the 3rd edition, (1999) John Wiley & Sons, Inc. can be referred to.

Step 3:

This step can be performed by dissolving Compound (IV) and an ester of dichloroacetic acid in a solvent such as THF, dioxane, 1,2-dimethoxyethane, dimethylformamide (DMF), and dimethyl sulfoxide (DMSO), adding a base such as sodium alkoxide, sodium hydride, or lithium diisopropylamide (LDA) to the solution under atmosphere of an inert gas, and stirring at room temperature or under heating for one hour to 24 hours.

Step 4:

This step is to deprotect the protected hydroxy group of Compound (V). As to condition for deprotection of the hydroxy group, "Protective Groups in Organic Synthesis," P. G. M. Wuts and T. W. Greene, the 3rd edition, (1999) John Wiley & Sons, Inc. can be referred to. In some compounds, the deprotection can be achieved in the following step 5 simultaneously, and for those compounds, this step 4 can be omitted.

Step 1:

Compound (IX) can be prepared by an esterification of Compound (VIII) according to an ordinary method. The esterification method is not particularly limited, and may be any appropriate method such as active esterification method, a mixed acid anhydride method, or a condensation method which are generally used.

Step 2:

Compound (IX) is dissolved in a solvent such as carbon tetrachloride, cyclohexane, or benzene. The solution is added with a halogenating agent such as N-bromosuccinimide, stirred at room temperature or under heating for one hour to 24 hours. Compound (X) can thus be obtained. For promotion of the reaction, a radical initiator such as dibenzoyl peroxide or azobisisobutyronitrile can be added to the reaction mixture.

Step 3:

Compound (X) is dissolved in water or a mixed solvent of water and organic solvent such as acetone, THF, and DMF. The solution is added with a silver salt such as silver nitrate or silver perchlorate, or a base such as sodium hydrogen carbonate, and stirred under cooling or under heating for one hour to 24 hours. Compound (XI) can thus be obtained.

Step 4:

This step can be achieved by the same method as that of the step 5 of the preparation route 1.

<Preparation Route 3>

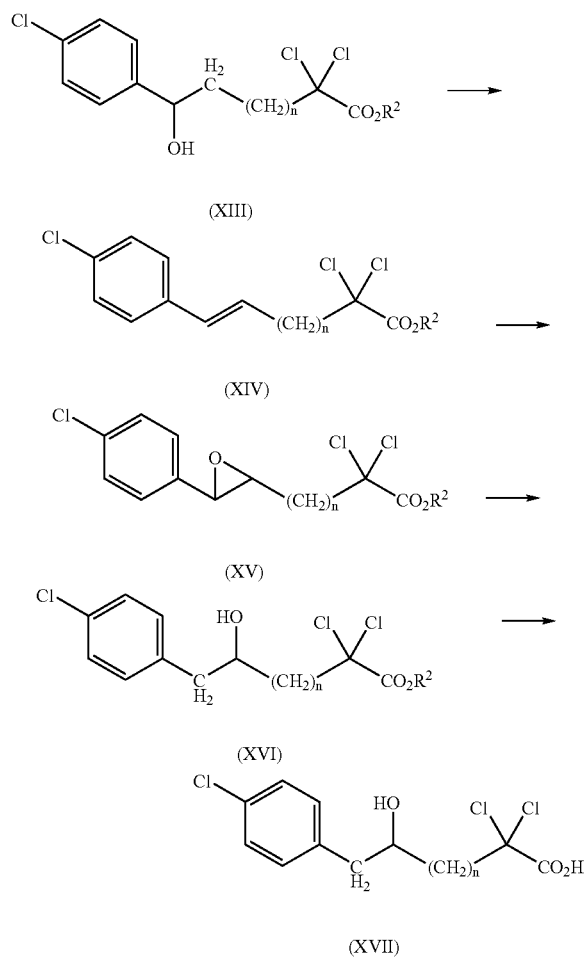

Step 1:

Compound (XIII), without a solvent or being dissolved in a solvent such as toluene, acetone, or DMSO, is added with an acid such as sulfuric acid, phosphoric acid, oxalic acid, or p-toluenesulfonic acid and stirred under cooling or under heating for one hour to 24 hours. Compound (XIV) can thus be obtained Step 2:

Compound (XIV) is dissolved in a solvent such as chloroform, methylene chloride, or diethyl ether. The solution or a mixed solution of the solution and aqueous sodium hydrogencarbonate solution is added with a peracid such as perbenzoic acid, 3-chloro perbenzoic acid, or trifluoroperacetic acid and stirred under cooling or under heating for one hour to 24 hours. Compound (XV) can thus be obtained Step 3:

Compound (XV) is dissolved in a solvent such as THF, ethyl acetate, alcohols, or acetic acid. The solution is added with a catalyst such as palladium on carbon or Raney nickel and stirred at atmospheric pressure or positive pressure under hydrogen atmosphere, and under cooling or under heating for one hour to 24 hours. Compound (XVI) can thus be obtained Step 4:

This step can be achieved by a similar method as that of the step 5 of the preparation route 1.

<Preparation route 4>

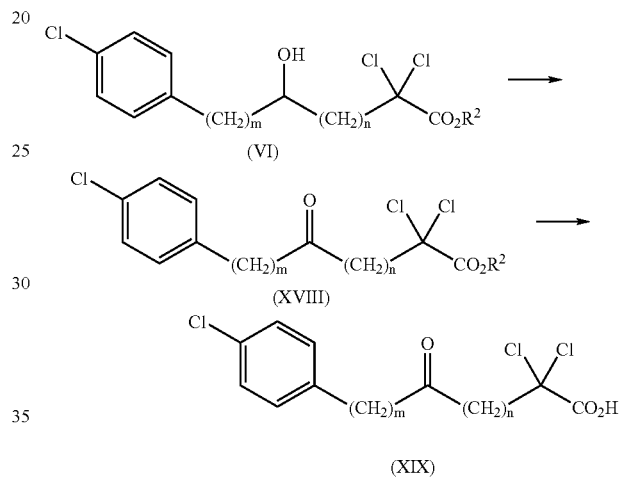

Step 1:

Compound (VI) is dissolved in a solvent such as dichloromethane, acetone, or diethyl ether. The solution is added with pyridinium chlorochromate (PCC), pyridinium dichromate (PDC), or the like, and stirred under cooling or under heating for one hour to 24 hours. This step can thus be achieved.

Step 2:

This step can be achieved by a similar method as that of the step 5 of the preparation route 1.

After the reactions of each of the aforementioned preparation routes from 1 to 4, post-treatment can be conducted according to an ordinary method, and the desired compound can be used as a starting material of the next step after an ordinary purification, if necessary.

Among the compound of the present invention, optically active compound can be obtained by a method for optical resolution of a racemate of the present invention or an intermediate thereof, or an asymmetric synthesis of a compound of the present invention or an intermediate thereof. As the method for optical resolution, examples include a resolution by using chromatography with optically active packing materials, resolution by using chromatography after a compound is converted to diastereomers, and recrystallization after a compound is converted to salts of diastereomers. As the asymmetric synthesis, examples include asymmetric oxidation, asymmetric reduction, and bond formation with an asymmetric carbon which are conducted by using an optically active reagent or catalyst, and reduction, hydrolysis, and esterification which are conducted by using biocatalyst such as an enzyme or an yeast.

The compounds of the present invention obtained through the aforementioned synthetic routes can be purified by ordinary purification methods such as recrystallization and column chromatography, if necessary. Further, if necessary, the compound of the present invention can be converted to any desired salts or solvates as mentioned above by an ordinary method. Methods for preparation of the compounds of the present invention are more specifically detailed in the examples of the specification. Accordingly, one of ordinary skill in the art can readily prepare any of the compounds according to the present invention by suitably choosing reagents, starting reaction materials, and reaction conditions by referring to the aforementioned general explanation of the preparation methods and specific explanations in the examples, and by optionally altering and modifying these methods.

As shown in the test examples described below, the compounds of the present invention or salts thereof exert potent reducing action of plasma glucose in vivo evaluation system. Therefore, the compounds of the present invention or salts thereof is useful as an active ingredient of a medicine for preventive and/or therapeutic treatment of diabetes, complications of diabetes, hyperlipemia, atherosclerosis and others. The medicine can be administered to mammals including human and has an excellent characteristic feature that the medicine causes no weight gain or obesity.

The medicine of the present invention comprises as an active ingredient a substance selected from the group consisting of a compound represented by the aforementioned general formula (1) [wherein m represents an integer of 0 to 4, n represents an integer of 5 to 9, and W represents —CH(OR)— (wherein R represents hydrogen atom or a protective group of hydroxyl group) or —C(=O)—], a physiologically acceptable salt thereof, and a physiologically acceptable ester thereof. As the medicine of the present invention, the aforementioned substance, per se, can be used. Generally, however, a pharmaceutical composition comprising the aforementioned substance and one or more pharmaceutical additives is preferred to be formulated for administration. As the medicine of the present invention, two or more of the aforementioned substances can be used in combination.

Administration routes of the medicine of the present invention are not particularly limited, and the medicine can be administered through either oral administration or parenteral administration. As a pharmaceutical composition suitable for oral administration, either solid or liquid pharmaceutical composition may be used. As a pharmaceutical composition suitable for parenteral administration, examples include formulation forms such as injections, drip infusions, suppositories, external preparations, eye drops, nasal drops, ear drops, and patches.

Solid pharmaceutical compositions for oral administration can be prepared as tablets, granules, powders, or capsules according to an ordinary method, for example, after excipients are added to the aforementioned substance as an active ingredient, or after pharmaceutical additives such as binders, disintegrants, lubricants, coloring agents, and flavoring substance are further added, if necessary. As the pharmaceutical additives, those generally used in the art can be used. Examples include excipients such as lactose, sodium chloride, glucose, starch, microcrystalline cellulose, and silica; binders such as water, ethanol, propanol, simple syrup, gelatin, hydroxypropylcellulose, methylcellulose, ethylcellulose, shellac, and polyvinylpyrrolidone; disintegrant such as agar powder, sodium laurylsulfate, and stearic acid monoglyceride; lubricants such as purified talc, stearates, borax, and polyethylene glycol; coloring agents such as β-carotene, yellow ferric oxide, and caramel; flavoring substances such as sucrose and orange peel.

Liquid pharmaceutical compositions for oral administration can be prepared as liquids for oral administration, syrups, elixirs and others, by addition of one or more pharmaceutical additives such as flavoring substances, stabilizing agents, and preservatives to the aforementioned substance as an active ingredient according to an ordinary method. As pharmaceutical additives, those generally used in the art can be used. Examples include flavoring substances such as sucrose; stabilizing agents such as tragacanth; preservatives such as paraoxybenzoates.

Injections can be prepared as injections for subcutaneous, intravascular, or intravenous administrations by addition of one or more pharmaceutical additives such as stabilizing agents and isotonizing agents to the aforementioned substance as an active ingredient according to an ordinary method. As pharmaceutical additives, those generally used in the art can be used. Examples include stabilizing agents such as sodium pyrosulfite; isotonizing agents such as sodium chloride.

Suppositories can be prepared by addition of pharmaceutical additives such as carriers and surfactants to the aforementioned substance as an active ingredient according to an ordinary method. As pharmaceutical additives, those generally used in the art can be used. Examples include carriers such as polyethylene glycol and hard fat; surfactants such as polysorbate 80.

External preparations can be prepared as a liquid agent, a cream agent, a gel agent, or an ointment by addition of one or more pharmaceutical additives such as base agents, water-soluble polymers, solvents, surfactants, and preservatives to the aforementioned substance as an active ingredient according to an ordinary method. As pharmaceutical additives, those generally used in the art can be used. Examples include base materials such as liquid paraffin, white petrolatum, and purified lanoline; water-soluble polymers such as carboxy vinyl polymer; solvents such as glycerol and water; surfactants such as polyoxyethylene fatty acid esters; and preservatives such as paraoxybenzoates.

Eye drops can be prepared by addition of one or more pharmaceutical additives such as stabilizing agents, isotonizing agents, and preservatives to the aforementioned substance as an active ingredient according to an ordinary method. As pharmaceutical additives, those generally used in the art can be used. Examples include stabilizing agents such as sodium pyrosulfite and EDTA; isotonizing agents such as sodium chloride; and preservatives such as chlorobutanol.

Nasal drops can be prepared by addition of one or more pharmaceutical additives such as stabilizing agents, isotonizing agents, and preservatives to the aforementioned substance as an active ingredient according to an ordinary method. As pharmaceutical additives, those generally used in the art can be used. Examples include stabilizing agents such as sodium pyrosulfite and EDTA; isotonizing agents such as sodium chloride; and preservatives such as benzalkonium chloride.

Ear drops can be prepared by addition of one or more pharmaceutical additives such as stabilizing agents, isotonizing agents, and preservatives to the aforementioned substance as an active ingredient according to an ordinary method. As pharmaceutical additives, those generally used in the art can be used. Examples include stabilizing agents such as sodium pyrosulfite and EDTA; isotonizing agents such as sodium chloride; and preservatives such as benzalkonium chloride.

Patches can be prepared as hydrous patches, plaster-type patches and the like, by addition of one or more pharmaceutical additives such as adhesives, solvents, crosslinking agents, and surfactants to the aforementioned substance as an active ingredient according to an ordinary method. As pharmaceutical additives, those generally used in the art can be used. Examples include adhesives such as partially neutralized polyacrylic acid, sodium polyacrylate, 2-ethylhexyl polyacrylate, and styrene-isoprene-styrene block copolymer; solvents such as glycerol and water; crosslinking agents such as aluminum dihydroxide aminoacetate and dried aluminium hydroxide gel; and surfactants such as polyoxyethylene fatty acid esters.

The dose of the medicine of the present invention is not particularly limited, and may be suitably chosen depending on the age, body weight, and condition of a patient, the administration form, the administration route, number of the administration and others. Generally, 0.1 to 100 mg, as the weight of the aforementioned substance as an active ingredient, can be administered per a day for an adult. The medicine of the present invention can be administered orally or parenterally, once a day or a few times a day as divided portions.

EXAMPLES

The present invention will be explained more specifically with reference to examples. However, the present invention is not limited to the following examples.

Example 1

(1) Preparation of 10-bromo-1-(4-chlorophenyl)-5-decanol

Magnesium (591 mg, 24.31 mmol) was added in 5 ml of anhydrous THF, and the mixture was stirred at room temperature under argon atmosphere. The mixture was added with iodine (10 mg) and further stirred for 2 hours until brown color was almost disappeared. The reaction mixture was added dropwise with 10 ml of anhydrous THF solution of 4-(4-bromobutyl) chlorobenzene (6.02 g, 24.32 mmol) over 10 minutes. The mixture was stirred at room temperature for 3 hours from the end of the dropping to prepare a Grignard reagent.

6-Bromohexanal (4.79 g, 49.58 mmol) was dissolved in 10 ml of anhydrous THF, and the mixture was stirred under ice cooling. The mixture was added dropwise with the above prepared Grignard reagent over 10 minutes. The reaction mixture was warmed up to room temperature, and continued to be stirred for 18 hours.

After the reaction was completed, the reaction mixture was slowly added with 20 ml of purified water and 20 ml of saturated brine under ice cooling, and stirred for 20 minutes. The mixture was extracted with diethyl ether (50 mL, 100 mL, 20 mL×2). Subsequently, the extract was washed once with 20 ml of purified water and once with 30 ml of saturated brine, dried over sodium sulfate, and concentrated under reduced pressure to obtain 16.54 g of pale green oil as a crude product. The oil was purified by silica gel column chromatography (eluent n-hexane/ethyl acetate=10/1) to obtain the desired compound (3.14 g, yield 37.1%) as colorless oil.

$^1$H-NMR (CDCl$_3$) δ: 1.23–1.67 (12H, m), 1.87 (2H, tt, J=7, 7 Hz), 2.59 (2H, t, J=8 Hz), 3.41 (2H, t, J=7 Hz), 3.58 (1H, m), 7.10 (2H, d, J=8 Hz), 7.24 (2H, d, J=8 Hz), (2) Preparation of 5-acetoxy-10-bromo-1-(4-chlorophenyl)decane 10-Bromo-1-(4-chlorophenyl)-5-decanol (3.14 g, 9.03 mmol), 4-dimethylaminopyridine (111 mg, 0.903 mmol), and pyridine (3.97 g, 18.1 mmol) were dissolved in 50 ml of dichloromethane. The solution was cooled with ice, stirred for 10 minutes, and then added dropwise with dichloromethane solution (50 ml) of acetyl chloride (851 mg, 10.8 mmol) over 10 minutes. The solution was further stirred at room temperature for 3 hours after the dropping was completed.

After the reaction was completed, the reaction mixture was slowly added with 20 mL of 2 mol/L hydrochloric acid and 20 mL of saturated brine under ice cooling, and stirred for 5 minutes. After the organic layer was separated, aqueous layer was further extracted twice, each with 100 mL of chloroform. The extracts were combined, washed once with 30 ml of purified water and once with 30 mL of saturated brine, dried over sodium sulfate, and then concentrated under reduced pressure to obtain 4.33 g of pale yellow oil as a crude product. The crude product was purified by silica gel flash column chromatography (eluent n-hexane/ethyl acetate=20/1) to obtain the desired compound (3.50 g, yield 99.4%) as colorless oil.

$^1$H-NMR (CDCl$_3$) 67 : 1.22–1.65 (12H, m), 1.84 (2H, tt, J=7, 7 Hz), 2.02 (3H, s), 2.56 (2H, t, J=8 Hz), 3.39 (2H, t, J=7 Hz), 4.85 (1H, m), 7.08 (2H, d, J=8 Hz), 7.24 (2H, d, J=8 Hz).

(3) Preparation of methyl 8-acetoxy-2,2-dichloro-12-(4-chlorophenyl) dodecanoate 5-Acetoxy-10-bromo-1-(4-chlorophenyl)decane (3.50 g, 8.97 mmol) was dissolved in 50 mL of DMF, and stirred under argon atmosphere at room temperature. The solution was added with methyl dichloroacetate (5.14 g, 35.9 mmol) and cooled with ice. The solution was added with sodium hydride (1.50 g, 35.9 mmol) as one portion, stirred for one hour, and further stirred at room temperature for 36 hours.

The reaction mixture was slowly added with 20 mL of saturated brine under ice cooling, and stirred for 5 minutes. The mixture was further added with 80 mL of water, extracted three times, each with 50 mL of diethyl ether. Subsequently, the extract was washed once with 50 mL of purified water and once with 50 mL of saturated brine, dried over sodium sulfate, and then concentrated under reduced pressure to obtain 6.24 g of pale yellow oil as a crude product. The crude product was purified by silica gel flash column chromatography (eluent n-hexane/ethyl acetate=20/1) to obtain the desired compound (1.43 g, yield 35.5%) as colorless oil.

$^1$H-NMR (CDCl$_3$) δ: 1.22–1.42 (6H, m), 1.46–1.66 (8H, m), 2.03 (3H, s), 2.40 (2H, m), 2.57 (2H, t, J=8Hz), 3.89 (3H, s), 4.85 (1H, m), 7.09 (2H, d, J=9 Hz), 7.23 (2H, d, J=9 Hz).

(4) Preparation of 2,2-dichloro-12-(4-chlorophenyl)-8-hydroxydodecanoic acid

Methyl 8-acetoxy-2,2-dichloro-12-(4-chlorophenyl) dodecanoate (1.43 g, 3.17 mmol) was dissolved in 40 mL of methanol, and stirred under ice cooling. The solution was added with 2 mol/L aqueous lithium hydroxide solution (15.9 mL, 31.7 mmol), stirred for 15 minutes, and further stirred at room temperature for 20 hours.

After the reaction was completed, the reaction mixture was added dropwise with 20 mL of saturated brine and 20 mL of 2 mol/L hydrochloric acid under ice cooling so as to be acidic, and then extracted three times, each with 100 mL of chloroform. Subsequently, the extract was washed once with 50 mL of purified water and once with 50 mL of saturated brine, dried over sodium sulfate, and then concentrated under reduced pressure to obtain 1.68 g of pale yellow oil as a crude product. The crude product was purified by silica gel column chromatography (eluent chloroform/methanol=20/1–2/1) to obtain the desired compound (749 mg, yield 59.7%) as pale yellow oil.

$^1$H-NMR (CDCl$_3$) δ: 1.24–1.77 (14H, m), 2.43 (2H, m), 2.58 (2H, t, J=8 Hz), 3.67 (1H, br), 7.09 (2H, d, J=8 Hz), 7.23 (2H, d, J=8 Hz).

Example 2

(1) Preparation of 10-bromo-1-(4-chlorophenyl)-3-decanol

Magnesium (1.07 g, 44.0 mmol) was added in 20 ml of anhydrous THF, and the solution was stirred at room temperature under argon atmosphere. The solution was added with iodine (10 mg) and further stirred for 2 hours until brown color almost disappeared. The reaction mixture was slowly added with 20 ml of anhydrous THF solution of 4-(2-bromoethyl) chlorobenzene (9.62 g, 43.8 mmol). The mixture was stirred for 3 hours to prepare a Grignard reagent.

8-Bromo-1-octanal (10.27 g, 49.6 mmol) was dissolved in 30 ml of anhydrous THF under argon atmosphere, and the solution was stirred under ice cooling. The solution was added dropwise with the above prepared Grignard reagent over 15 minutes. The reaction mixture was warmed up to room temperature, and continued to be stirred for 16 hours.

After the reaction was completed, the reaction mixture was slowly added with 20 ml of purified water and 20 ml of saturated brine under ice cooling, and stirred for 20 minutes. The mixture was extracted twice, each with 100 mL of diethyl ether. Subsequently, the extract was washed once with 30 ml of purified water and once with 30 ml of saturated brine, dried over sodium sulfate, and then concentrated under reduced pressure to obtain 16.54 g of pale green oil as a crude product. The oil was purified by silica gel column chromatography (eluent n-hexane/ethyl acetate=8/1–4/1) to obtain the desired compound (5.85 g, yield 38.3%) as colorless oil.

$^1$H-NMR (CDCl$_3$) δ: 1.23–1.76 (12H, m), 1.80–1.88 (2H, m), 2.56–2.69 (1H, m), 2.70–2.81 (1H, m), 3.40 (2H, t, J=7 Hz), 3.51–3.66 (1H, m), 7.12 (2H, d, J=9 Hz), 7.24 (2H, d, J=9 Hz).

(2) Preparation of 3-acetoxy-10-bromo-1-(4-chlorophenyl)decane

10-Bromo-1-(4-chlorophenyl)-3-decanol (5.85 g, 16.8 mmol) was dissolved in 50 ml of dichloromethane. The solution was cooled with ice, added with 4-dimethylaminopyridine (205 mg, 1.68 mmol) and pyridine (7.38 g, 33.62 mmol), and stirred for 10 minutes. The solution was added dropwise with dichloromethane solution (50 ml) of acetyl chloride (1.58 g, 20.13 mmol) over 5 minutes, and the mixture was stand with stirring for 20 minutes, and further stirred at room temperature for 30 minutes.

After the reaction was completed, the reaction mixture was slowly added with 20 mL of 2 mol/L hydrochloric acid and 20 mL of saturated brine under ice cooling, and stirred for 5 minutes. The mixture was extracted twice, each with 200 mL of ethyl acetate. Subsequently, the extract was washed once with 30 ml of purified water and once with 30 mL of saturated brine, dried over sodium sulfate, and then concentrated under reduced pressure to obtain 7.02 g of pale yellow oil as a crude product. The crude product was purified by silica gel column chromatography (eluent n-hexane/ethyl acetate=20/1) to obtain the desired compound (5.17 g, yield 78.8%) as colorless oil.

$^1$H-NMR (CDCl$_3$) δ: 1.24–1.60 (10H, m), 1.76–1.89 (4H, m), 2.04 (3H, s), 2.51–2.68 (2H, m), 3.40 (2H, t, J=7 Hz), 4.86–4.94 (1H, m), 7.10 (2H, d, J=8 Hz), 7.24 (2H, d, J=8 Hz).

(3) Preparation of methyl 10-acetoxy-2,2-dichloro-12-(4-chlorophenyl) dodecanoate 3-Acetoxy-10-bromo-1-(4-chlorophenyl)decane (5.17 g, 13.26 mmol) was dissolved in 50 mL of DMF, and stirred under argon atmosphere at room temperature. The solution was added with methyl dichloroacetate (5.69 g, 39.80 mmol), stirred for 10 minutes, and further stirred at −10° C. for 10 minutes. The solution was rapidly added with sodium hydride (1.74 g, 39.79 mmol), stirred for one hour, and further stirred at room temperature for 15 hours.

After the reaction was completed, the reaction mixture was slowly added with 20 mL of saturated brine under ice cooling, and stirred for 5 minutes. The mixture was extracted twice, each with 200 mL of diethyl ether. Subsequently, the extract was washed once with 30 mL of purified water and once with 30 mL of saturated brine, dried over sodium sulfate, and then concentrated under reduced pressure to obtain 6.39 g of pale yellow oil as a crude product. The crude product was purified by silica gel column chromatography (eluent n-hexane/ethyl acetate=20/1) to obtain the desired compound (1.68 g, yield 28.0%) as pale yellow oil.

$^1$H-NMR (CDCl$_3$) δ: 1.22–1.65 (12H, m), 1.76–1.92 (2H, m), 2.04 (3H, s), 2.37–2.46 (2H, m), 2.50–2.66 (2H, m), 3.89 (3H, s), 4.86–4.96 (1H, m), 7.10 (2H, d, J=9 Hz), 7.24 (2H, d, J=9Hz).

(4) Preparation of 2,2-dichloro-12-(4-chlorophenyl)-10-hydroxydodecanoic acid

Methyl 10-acetoxy-2,2-dichloro-12-(4-chlorophenyl) dodecanoate (1.68 g, 3.72 mmol) was dissolved in 40 mL of methanol, and stirred under ice cooling. The solution was added with 2 mol/L aqueous lithium hydroxide solution (18.6 mL, 37.2 mmol), stirred for 10 minutes, and further stirred at room temperature for 16 hours.

After the reaction was completed, the reaction mixture was added dropwise with 20 mL of saturated brine and 20 mL of 2 mol/L hydrochloric acid under ice cooling so as to be acidic, and extracted three times, each with 150 mL of chloroform. Subsequently, the extract was washed once with 30 mL of purified water and once with 30 mL of saturated brine, dried over sodium sulfate, and then concentrated under reduced pressure to obtain as a crude product 1.68 g of pale yellow oil.

The oil was purified by silica gel column chromatography (eluent chloroform/methanol=10/1–2/1). The fraction containing the desired compound was concentrated under reduced pressure, and the residue was dissolved in 300 mL of chloroform. The solution was washed with mixed solution of 30 mL of saturated brine and 30 mL of 2 mol/L hydrochloric acid, and subsequently, washed once with 50 mL of purified water and once with 50 mL of saturated brine. The solution was dried over sodium sulfate and concentrated under reduced pressure to obtain 1.32 g of colorless oil as a crude product. The oil was added with n-hexane for crystallization to obtain 1.30 g of white crystalline powders. The crude crystals were recrystallized from a mixed solvent of ethyl acetate-n-hexane to obtain the desired compound (1.00 g, yield 67.9%) as white crystalline powders $^1$H-NMR (CDCl$_3$) δ: 1.26–1.52 (10H, m), 1.54–1.63 (2H, m), 1.71–1.79 (2H, m), 2.41–2.47(2H, m), 2.60–2.69 (1H, m), 2.72–2.81 (1H, m), 3.67 (1H, br), 7.12 (2H, d, J=8 Hz), 7.25 (2H, d, J=8 Hz).

Melting point: 100.0–101.7° C. (solvent for recrystallization: ethyl acetate-n-hexane)

Example 3

(1) Preparation of methyl 2,2-dichloro-12-(4-chlorophenyl) dodecanoate 2,2-Dichloro-12-(4-chlorophenyl) dodecanoic acid (47.3 g, 124.5 mmol) was dissolved in 1000 ml of methanol. The solution was added with sulfuric acid (6.10 g, 62.19 mmol), and heated under reflux for 24 hours.

After cooling, the reaction mixture was concentrated under reduced pressure, and added with 500 mL of chloroform and 500 mL of water, and the organic layer was separated. The aqueous layer was further extracted with chloroform (100 mL×3). The organic layers were combined, washed with water (200 mL), dried over anhydrous sodium sulfate, and then evaporated under reduced pressure to obtain a crude product of the desired compound (47.35 g, yield 96.6%) as pale yellow oil.

$^1$H-NMR (CDCl$_3$) δ: 1.22–1.40 (12H, m), 1.51–1.62 (4H, m), 2.41(2H, m), 2.56 (2H, t, J=8 Hz), 3.89 (3H, s), 7.10 (2H, d, J=8 Hz), 7.23 (2H, d, J=8 Hz).

(2) Preparation of methyl 12-bromo-2,2-dichloro-12-(4-chlorophenyl) dodecanoate

The crude methyl 2,2-dichloro-12-(4-chlorophenyl) dodecanoate (47.25 g, 120.0 mmol) was dissolved in 500 ml of carbon tetrachloride. The solution was added with N-bromosuccinimide (22.42 g, 126.0 mmol) and 2,2-azoisobutyronitrile (39.4 mg, 0.25 mmol) and heated under reflux with stirring under argon atmosphere for one hour. After cooling, the reaction mixture was concentrated under reduced pressure. The residue was dissolved in 800 mL of ethyl acetate. The solution was washed with water (200 mL×3) and saturated brine (200 mL), and dried over anhydrous sodium sulfate. The solvent was evaporated under reduced pressure to obtain a crude product of the desired compound (57.35 g, quantitative) as pale yellow oil. $^1$H-NMR (CDCl$_3$) δ: 1.22–1.62 (14H, m), 2.10 (1H, m), 2.24 (1H, m), 2.41 (2H, m), 3.89 (3H, s), 4.90 (1H, t, J=7 Hz), 7.30 (2H, d, J=9Hz).

The crude methyl 12-bromo-2,2-dichloro-12-(4-chlorophenyl) dodecanoate (57.35 g ,120.0 mmol) was dissolved in a mixed solvent of acetone (1000 mL) and water (200 mL). The solution was added dropwise with 40% aqueous silver perchlorate (68.4 mL, 132 mmol) over 10 minutes at room temperature, and stirred at room temperature for 90 minutes after the dropping was completed. The reaction mixture was added with 200 mL of saturated brine, stirred for 30 minutes, and the insoluble solids were removed by filtration. Acetone was removed from the filtrate under reduced pressure, and the residue was combined with 500 mL of ethyl acetate that was used for washing the insoluble solids. Then, the organic layer was separated. The aqueous layer was further extracted with ethyl acetate (200 mL×2), and the organic layer was washed with water (200 mL) and saturated brine (200 mL). The resulting organic layer was dried over anhydrous sodium sulfate, and the solvent was evaporated under reduced pressure. The residue was purified by silica gel column chromatography (eluent n-hexane/acetone=8/1–2/1) to obtain the desired compound (28.97 g, yield 58.9%) as pale yellow oil.

$^1$H-NMR (CDCl$_3$) δ: 1.22–1.44 (12H, m), 1.51–1.83 (4H, m), 2.40 (2H, m), 3.89 (3H, s), 4.65 (1H, br), 7.27 (2H, d, J=6 Hz), 7.32 (2H, d, J=6 Hz).

(4) Preparation of 2,2-dichloro-12-(4-chlorophenyl)-12-hydroxydodecanoic acid

Methyl 2,2-dichloro-12-(4-chlorophenyl)-12-hydroxydodecanoate (28.88 g, 70.48 mmol) was dissolved in 300 mL of methanol, added with 2 mol/L aqueous lithium hydroxide solution (70.5 mL, 141 mmol) and stirred at room temperature for one hour. After methanol was evaporated under reduced pressure from the reaction mixture, the mixture was added with 200 mL of water and added dropwise with 2 mol/L hydrochloric acid under ice cooling so as to be acidic.

The mixture was added with 800 mL of a mixed solvent of chloroform-methanol (10:1), and the organic layer was separated. The aqueous layer was further extracted with a mixed solvent of chloroform-methanol (10:1) (200 mL×3). The organic layer was washed with water (100 mL) and saturated brine (100 mL), and dried over anhydrous sodium sulfate. The solvent was evaporated under reduced pressure to obtain colorless oil. The oil was added with a seed crystal, and dried under stirring under reduced pressure to obtain a crude product of the desired compound (27.80 g) as white crystalline powders. The powders were recrystallized from a mixed solvent of diethyl ether-n-hexane to obtain the desired compound (16.00 g, yield 57.4%) as white crystalline powders.

$^1$H-NMR (CDCl$_3$) δ: 1.22–1.45 (12H, m), 1.57 (2H, m), 1.68 (1H, m), 1.78 (1H, m), 2.45 (2H, m), 4.03–5.01 (1H, br), 4.70 (1H, dd, J=8, 6 Hz), 7.27 (2H, d, J=9 Hz), 7.32 (2H, d, J=9Hz).

Melting point: 62.2–63.5° C. (solvent for recrystallization: diethyl ether-n-hexane)

Example 4

(1) Preparation of methyl 2,2-dichloro-12-(4-chlorophenyl)-11-dodecenoate

Methyl 2,2-dichloro-12-(4-chlorophenyl)-12-hydroxydodecanoate (8.89 g, 21.91 mmol) was dissolved in 300 ml of toluene. The solution was added with p-toluenesulfonic acid monohydrate (1.67 g, 8.78 mmol), and stirred at 80° C. for 4 hours. The reaction mixture was washed with 200 mL of water and 10 ml of aqueous saturated sodium hydrogencarbonate. The aqueous layer was further extracted with 100 mL of ethyl acetate. The organic layers were combined, washed with saturated brine, and dried over anhydrous sodium sulfate. The extracts were purified by silica gel column chromatography (eluent: ethyl acetate/n-hexane=1/1). The solvent was evaporated under reduced pressure to obtain the desired compound (8.38 g, yield 97.6%) as yellow oil.

$^1$H-NMR (CDCl3) δ:1.24–1.41(8H, m), 1.42–1.51(2H, m), 1.52–1.63(2H, m), 2.14–2.25 (2H, m), 2.37–2.48 (2H, m), 3.89 (3H, s), 6.20 (1H, dt, J=16, 7 Hz), 6.32 (1H, d, J=16 Hz), 7.22–7.30 (4H, m).

(2) Preparation of methyl 2,2-dichloro-12-(4-chlorophenyl)-11,12-epoxydodecanoate Methyl 2,2-dichloro-12-(4-chlorophenyl) 11-dodecenoate (8.38 g, 21.39 mmol) was dissolved in 200 ml of chloroform. The solution was added with 3-chloroperbenzoic acid (7.38 g, 42.77 mmol) and stirred at room temperature for two hours. The reaction mixture was washed with 200 mL of 5% aqueous sodium thiosulfate and 200 mL of saturated brine in order, and dried over anhydrous sodium sulfate. The solvent was evaporated under reduced pressure to obtain a residue (12.24 g) as pale yellow crystals. The residue was purified by silica gel column chromatography (eluent n-hexane/chloroform=1/9) to obtain the desired compound (8.30 g, yield 95.2%) as colorless oil.

$^1$H-NMR (CDCl$_3$) δ: 1.23–1.41 (8H, m), 1.42–1.62 (4H, m), 1.62–1.72 (2H, m), 2.36–2.46 (2H, m), 2.89 (1H, td, J=6, 2 Hz), 3.58 (1H, d, J=2Hz), 3.89 (3H, s), 7.16–7.22 (2H, d, J=9 Hz), 7.28–7.33 (2H, d, J=9 Hz).

(3) Preparation of methyl 2,2-dichloro-12-(4-chlorophenyl)-11-hydroxydodecanoate Methyl 2,2-dichloro-12-(4-chlorophenyl)-11,12-epoxydodecanoate (6.87 g, 16.85 mmol) was dissolved in 200 mL of ethyl acetate. The solution was added with 10% palladium on carbon catalyst (1.37 g) at −12° C., and stirred under hydrogen gas atmosphere at the same temperature for one hour. The palladium on carbon was removed by filtration, and the solids on the filter were washed with 60 mL of ethyl acetate. The filtrate was evaporated under reduced pressure to obtain a residue as colorless oil (6.89 g). The residue was purified by silica gel column chromatography (eluent n-hexane/ethyl acetate=8/1–4/1) to obtain the desired compound (6.27 g, yield 90.8%) as colorless oil.

$^1$H-NMR (CDCl$_3$) d:1.23–1.64 (14H, m), 2.36–2.46 (2H, m), 2.63 (1H, dd, J=14, 8 Hz), 2.79 (1H, dd, J=14, 4 Hz), 3.79 (1H, m), 3.89 (3H, s), 7.15 (2H, d, J=8 Hz), 7.28 (2H, d, J=8 Hz).

(4) Preparation of 2,2-dichloro-12-(4-chlorophenyl)-11-hydroxydodecanoic acid

Methyl 2,2-dichloro-12-(4-chlorophenyl)-11-hydroxydodecanoate (4.62 g, 11.27 mmol) was dissolved in 25 mL of methanol. The solution was added dropwise with 2 mol/L aqueous lithium hydroxide solution (11.3 mL, 22.60 mmol) under ice cooling over about 5 minutes, and stirred at the same temperature for 30 minutes. The reaction mixture was added with 75 mL of saturated brine, and further added dropwise with 15 mL of 2 mol/L hydrochloric acid under ice cooling so as to be acidic, and then extracted with chloroform (50 mL, 20 mL×2). The organic layers were combined, washed with 100 mL of saturated brine, and dried over anhydrous sodium sulfate, and the solvent was evaporated under reduced pressure. The residue was added with 100 mL of n-hexane and the solution was stirred under ice cooling for crystallization. The crystals were removed by filtration, washed with n-hexane, and dried in the air to obtain 4.41 g of colorless crystalline powders. The crystals were recrystallized from a mixed solvent of ethyl acetate (5 mL)-n-hexane (40 mL) to obtain the desired compound (4.01 g, yield 89.9%) as colorless fine needles.

$^1$H-NMR (CDCl3) δ:1.24–1.42 (10H, m), 1.42–1.65 (4H, m), 2.38–2.48 (2H, m), 2.67 (1H, dd, J=14, 8 Hz), 2.81 (1H, dd, J=14, 4 Hz), 3.86 (1H, m), 7.15 (2H, d, J=8 Hz), 7.27 (2H, d, J=8 Hz).

Melting point: 84.1–85.8° C. (solvent for recrystallization: ethyl acetate-n-hexane)

Example 5

(1) Preparation of 3-benzoyloxy-10-bromo-1-(4-chlorophenyl)decane

The desired compound (211 mg, yield 82.8%) was obtained as colorless oil in a similar method to that of Example 2 (2) from 10-bromo-1-(4-chlorophenyl)-3-decanol (196 mg, 0.564 mmol) and benzoyl chloride (95 mg, 0.676 mmol).

$^1$H-NMR (CDCl$_3$) δ: 1.24–1.80 (12H, m), 1.80–2.09 (2H, m), 2.57–2.76 (2H, m), 3.34 (2H, t, J=7 Hz), 5.11–5.22 (1H, m), 7.09 (2H, d, J=9 Hz), 7.21 (2H, d, J=9 Hz), 7.44 (2H, t, J=7 Hz), 7.56 (1H, t, J=7 Hz), 8.02 (2H, d, J=7 Hz).

(2) Preparation of methyl 10-benzoyloxy-2,2-dichloro-12-(4-chlorophenyl) dodecanoate The desired compound (31.3 mg, yield 23.7%) was obtained as colorless oil in a similar method to that of Example 2 (3) from 3-benzoyloxy-10-bromo-1-(4-chlorophenyl) decane (116 mg, 0.257 mmol).

$^1$H-NMR (CDCl$_3$) δ: 1.15–1.82 (12H, m), 1.82–2.11 (2H, m), 2.33–2.44 (2H, m), 2.58–2.76 (2H, m), 3.88 (3H, s), 5.11–5.22 (1H, m), 7.10 (2H, d, J=9 Hz), 7.22 (2H, d, J=9 Hz), 7.45 (2H, t, J=7 Hz), 7.57 (1H, t, J=7 Hz), 8.02 (2H. d, J=7 Hz).

(3) Optical resolution of methyl 10-benzoyloxy-2,2-dichloro-12-(4-chlorophenyl) dodecanoate A racemate of 10-benzoyloxy-2,2-dichloro-12-(4-chlorophenyl) dodecanoate (1.28 g) was subjected to optical resolution by high performance liquid chromatography (HPLC) by using optically active column (column; Chiralcel OJ manufactured by Daicel chemical industries, Ltd., moving phase n-hexane: 2-propanol 19:1).

(a) Fractions containing only a product that gave a peak at with an earlier retention time were combined and concentrated under reduced pressure. The residue was purified again by flash column chromatography (eluent: n-hexane/ethyl acetate=20/1–10/1), and (+)-methyl 10-benzoyloxy-2,2-dichloro-12-(4-chlorophenyl) dodecanoate (the product that gave the peak with the earlier retention time in the optically active column, Chiralcel OJ) (449 mg, yield 35.1%) was obtained as colorless oil. Optical purity based on a ratio of HPLC peak area: >99% ee (Chiralcel OJ, moving phase: n-hexane/2-propanol=19/1) Specific rotation: $[α]_D^{27}$=+8.23 (c 1.15, CHCl$_3$)

(b) Fractions containing only a product that gave a peak with a later retention time were combined and concentrated under reduced pressure. The residue was purified again by flash column chromatography (eluent: n-hexane/ ethyl acetate=20/1–10/1), and (–)-methyl 10-benzoyloxy-2,2-dichloro-12-(4-chlorophenyl) dodecanoate (the product that gave the peak with the later retention time in the optically active column, Chiralcel OJ) (432 mg, yield 33.8%) was obtained as colorless oil.

Optical purity based on a ratio of HPLC peak area: >99% ee (Chiralcel OJ, moving phase: n-hexane/2-propanol=19/1)
Specific rotation: $[\alpha]_D^{27}$=–8.06 (c 1.10, CHCl$_3$)

(4) Preparation of (+)-2,2-dichloro-12-(4-chlorophenyl)-10-hydroxydodecanoic acid The desired compound (19.58 g, yield 57.5%) was obtained as white crystalline powders in a similar method to that of Example 2 (4) from (+)-methyl 10-benzoyloxy-2,2-dichloro-12-(4-chlorophenyl) dodecanoate (the product that gave the peak with the earlier retention time in the optically active column, Chiralcel OJ, >99% ee) (44.2 g, 86.0 mmol).
Melting point: 103.1–103.6° C. (solvent for recrystallization: ethyl acetate-n-hexane)
$^1$H-NMR (CDCl$_3$) δ: 1.26–1.63 (12H, m), 1.71–1.79 (2H, m), 2.38–2.47 (2H, m), 2.58–2.69 (1H, m), 2.70–2.80 (1H, m), 3.68 (1H, br), 7.12 (2H, d, J=8 Hz), 7.24 (2H, d, J=8 Hz).

Optical purity based on a ratio of HPLC peak area: >99% ee (Chiralpak AD-RH, moving phase: acetonitrile/5 mM H$_3$PO$_4$ buffer=70/30)
Specific rotation: $[\alpha]_D^{23}$=+8.06 (c 5.00, CHCl$_3$)

(5) Preparation of (–)-2,2-dichloro-12-(4-chlorophenyl)-10-hydroxydodecanoic acid The desired compound (20.59 g, yield 60.4%) was obtained as white crystalline powders in a similar method to that of the above (4) from (–)-methyl 10-benzoyloxy-2,2-dichloro-12-(4-chlorophenyl) dodecanoate (the product that gave the peak with the later retention time in the optically active column, Chiralcel OJ, >99% ee) (44.3 g, 86.2 mmol).
Melting point: 103.0–103.7° .C (solvent for recrystallization: ethyl acetate-n-hexane)
$^1$H-NMR (CDCl$_3$) δ: 1.19–1.63 (12H, m), 1.68–1.85 (2H, m), 2.38–2.47 (2H, m), 2.58–2.68 (1H, m), 2.70–2.81 (1H, m), 3.68 (1H, br), 7.12 (2H, d, J=9 Hz), 7.24 (2H, d, J=9 Hz).

Optical purity based on a ratio of HPLC peak area: >99% ee (Chiralpak AD-RH, moving phase: acetonitrile/5 mM H$_3$PO$_4$ buffer=70/30)
Specific rotation: $[\alpha]_D^{23}$=–8.02 (c 5.00, CHCl$_3$)

Example 6

(1) Preparation of 10-bromo-1-(4-chlorophenyl)-5-methoxymethoxydecane

10-Bromo-1-(4-chlorophenyl)-5-decanol obtained in Example 1 (1) (14.51 g, 41.7 mmol) and diisopropylethylamine (10.78 g, 83.4 mmol) were dissolved in 200 mL of chloroform and the solution was stirred under ice-cooling. The solution was added dropwise with chloromethylmethyl ether (5.04 g, 62.6 mmol), stirred under ice-cooling for one hour, and further stirred at room temperature for 30 hours.

The reaction mixture was added slowly with 100 mL of 2 mol/L hydrochloric acid under ice cooling and stirred, and then the organic layer was separated. After the aqueous layer was further extracted with chloroform (50 mL×2), the organic layers were combined, washed once with 50 mL of purified water, subsequently once with 50 mL of saturated brine, dried over sodium sulfate, and concentrated under reduced pressure. The residue was purified by silica gel flash column chromatography (eluent: n-hexane/ethyl acetate=20/1) to obtain the desired compound (13.30 g, yield 81.4%) as colorless oil.
$^1$H-NMR (CDCl$_3$) δ: 1.22–1.66 (12H, m), 1.86 (2H, quint., J=7 Hz), 2.58 (2H, t, J=8 Hz), 3.36 (3H, s), 3.41 (2H, t, J=7 Hz), 3.52 (1H, quint., J=7 Hz), 4.63 (2H, s), 7.09 (2H, d, J=8 Hz), 7.23 (2H, d, J=8 Hz).

(2) Preparation of methyl 2,2-dichloro-12-(4-chlorophenyl)-8-methoxymethoxydodecanoate The desired compound (4.02 g, yield 26.1%) was obtained as colorless oil in a similar method to that of Example 1 (3) from 10-bromo-1-(4-chlorophenyl)-5-methoxymethoxydecane (13.30 g, 33.95 mmol) and methyl dichloroacetate (19.42 g, 135.8 mmol).
$^1$H-NMR (CDCl$_3$) δ: 1.25–1.64 (14H, m), 2.38–2.44 (2H, m), 2.58 (2H, t, J=8 Hz), 3.36 (3H, s), 3.51 (1H, quint., J=6 Hz), 3.89 (3H, s), 4.63 (2H, s), 7.09 (2H, d, J=9 Hz), 7.23 (2H, d, J=9 Hz).

(3) Preparation of methyl 2,2-dichloro-12-(4-chlorophenyl)-8-hydroxydodecanoate

2 ,2-Dichloro-12-(4-chlorophenyl)-8-methoxymethoxydodecanoate (4.02 g, 8.86 mmol) was dissolved in 150 mL of methanol, and the solution was stirred under ice cooling. The mixture was added with 0.2 mL of hydrochloric acid, stirred under ice cooling for 15 minutes, and further stirred at room temperature for 20 hours.

The reaction mixture was evaporated under reduced pressure, and the residue was added with 100 mL of chloroform and 100 mL of purified water, and then the organic layer was separated. After the aqueous layer was further extracted with chloroform (20 mL×3), the organic layers were combined, washed once with 50 mL of purified water and once with 50 mL of saturated brine, dried over sodium sulfate, and concentrated under reduced pressure. The residue was purified by silica gel flash column chromatography (eluent: n-hexane/ethyl acetate=10/1–5/1) to obtain the desired compound (2.93 g, yield 80.7%) as colorless oil.
$^1$H-NMR (CDCl$_3$) δ: 1.22–1.51 (10H, m), 1.54–1.67 (4H, m), 2.39–2.45 (2H, m), 2.59 (2H, t, J=8 Hz), 3.58 (1H, m), 3.89 (3H, s), 7.10 (2H, d, J=9 Hz), 7.24 (2H, d, J=9 Hz).

(4) Preparation of methyl 2,2-dichloro-12-(4-chlorophenyl)-8-oxododecanoate

Methyl 2,2-dichloro-12-(4-chlorophenyl)-8-hydroxydodecanoate (1.50 g, 3.66 mmol) was dissolved in 50 mL of methylene chloride, and the solution was stirred under ice cooling. The mixture was slowly added with pyridinium chlorochromate (PCC) (1.58 g, purity 98%, 7.33 mmol), stirred under ice cooling for 30 minutes, and further stirred at room temperature for 3 hours.

The reaction mixture was added slowly with 100 mL of diethyl ether under ice cooling and stirred for 10 minutes. The mixture, per se, was subjected to silica gel column chromatography (eluent chloroform) to remove polar substances, and the solvent was evaporated under reduced pressure. The residue was further purified by silica gel flash column chromatography (eluent: n-hexane/ethyl acetate=20/1–10/1) to obtain the desired compound (1.35 g, yield 90.4%) as pale yellow oil.

$^1$H-NMR (CDCl$_3$) δ: 1.35 (2H, quint., J=8 Hz), 1.53–1.65 (8H, m), 2.36–2.44 (6H, m), 2.58(2H, t, J=7 Hz), 3.89 (3H, s), 7.09 (2H, d, J=8 Hz), 7.23 (2H, d, J=8 Hz).

(5) Preparation of 2,2-dichloro-12-(4-chlorophenyl)-8-oxododecanoic acid

The desired compound (1.15 g, yield 88.2%) was obtained as white crystalline powders in a similar method to that of Example 1 (4) from methyl 2,2-dichloro-12-(4-chlorophenyl)-8-oxododecanoate (1.35 g, 3.31 mmol).
Melting point: 48.8–49.7° C. (solvent for recrystallization: ethyl acetate-n-hexane)
$^1$H-NMR (CDCl$_3$) δ: 1.37(2H, quint., J=8 Hz), 1.53–1.68 (8H, m), 2.38–2.46(6H, m), 2.58(2H, t, J=7 Hz), 7.09(2H, d, J=9 Hz), 7.23(2H, d, J=9 Hz).

Example 7

(1) Preparation of 10-bromo-1-(4-chlorophenyl)-3-methoxymethoxydecane

The desired compound (5.73 g, yield 87.7%) was obtained as colorless oil in a similar method to that of Example 6 (1) from 10-bromo-1-(4-chlorophenyl)-3-decanol (5.80 g, 16.7 mmol) obtained in Example 2 (1) and chloromethylmethyl ether (4.04 g, 40.1 mmol).
$^1$H-NMR (CDCl$_3$) δ: 1.25–1.60 (10H, m), 1.72–1.89 (4H, m), 2.61 (1H, m), 2.70 (1H, m), 3.40 (3H, s), 3.50–3.59 (3H, m), 4.65 (1H, d, J=7 Hz), 4.68 (1H, d, J=7 Hz), 7.12 (2H, d, J=8 Hz), 7.24 (2H, d, J=8 Hz).

(2) Preparation of methyl 2,2-dichloro-12-(4-chlorophenyl)-10-methoxymethoxydodecanoate The desired compound (645 mg, yield 9.8%) was obtained as pale yellow oil in a similar method to that of Example 1 (3) from 10-bromo-1-(4-chlorophenyl)-3-methoxymethoxydecane (5.70 g, 14.6 mmol) and methyl dichloroacetate (6.23 g, 43.6 mmol).
$^1$H-NMR (CDCl$_3$) δ: 1.23–1.79 (14H, m), 2.41 (2H, m), 2.61 (1H, m), 2.70 (1H, m), 3.40 (3H, s), 3.56 (1H, m), 3.89 (3H, s), 4.65 (1H, d, J=7 Hz), 4.68 (1H, d, J=7 Hz), 7.12 (2H, d, J=8 Hz), 7.24 (2H, d, J=8 Hz).

(3) Preparation of methyl 2,2-dichloro-12-(4-chlorophenyl)-10-hydroxydodecanoate The desired compound (842 mg, yield 85.6%) was obtained as colorless oil in a similar method to that of Example 6 (3) from 2,2-dichloro-12-(4-chlorophenyl)-10-methoxymethoxydodecanoate (1.09 g, 2.40 mmol).
$^1$H-NMR (CDCl$_3$) δ: 1.23–1.63 (12H, m), 1.64–1.82 (2H, m), 2.41 (2H, m), 2.64 (1H, m), 2.77 (1H, m), 3.60 (1H, m), 3.89 (3H, s), 7.13 (2H, d, J=8 Hz), 7.24 (2H, d, J=8 Hz).

(4) Preparation of methyl 2,2-dichloro-12-(4-chlorophenyl)-10-oxododecanoate

The desired compound (749 mg, yield 89.6%) was obtained as colorless oil in a similar method to that of Example 6 (4) from methyl 2,2-dichloro-12-(4-chlorophenyl)-10-hydroxydodecanoate (840 mg, 2.05 mmol).
$^1$H-NMR (CDCl$_3$) δ: 1.19–1.42 (6H, m), 1.49–1.61 (4H, m), 2.37 (2H, t, J=8 Hz), 2.40 (2H, m), 2.70 (2H, t, J=8 Hz), 2.86 (2H, t, J=8 Hz), 3.89 (3H, s), 7.12 (2H, d, J=8 Hz), 7.23 (2H, d, J=8 Hz).

(5) Preparation of 2,2-dichloro-12-(4-chlorophenyl)-10-oxododecanoic acid

The desired compound (567 mg, yield 79.9%) was obtained as pale yellow oil in a similar method to that of Example 1 (4) from methyl 2,2-dichloro-12-(4-chlorophenyl)-10-oxododecanoate (735 mg, 1.80 mmol).
$^1$H-NMR (CDCl$_3$) δ: 1.19–1.42 (6H, m), 1.47–1.65 (4H, m), 2.39 (2H, m), 2.43 (2H, m), 2.71 (2H, t, J=8 Hz), 2.86 (2H, t, J=8 Hz), 7.11 (2H, d, J=8 Hz), 7.24 (2H, d, J=8 Hz).

Example 8

(1) Preparation of methyl 2,2-dichloro-12-(4-chlorophenyl)-11-oxododecanoate

The desired compound (4.36 g, yield 86.6%) was obtained as colorless oil in a similar method to that of Example 6 (4) from methyl 2,2-dichloro-12-(4-chlorophenyl)-11-hydroxydodecanoate obtained in Example 4 (3) (5.06 g, 12.35 mmol).
$^1$H-NMR (CDCl$_3$) δ: 1.17–1.38 (8H, m), 1.49–1.61 (4H, m), 2.36–2.42 (2H, m), 2.44 (2H, t, J=7 Hz), 3.65 (2H, s), 3.89 (3H, s), 7.13 (2H, d, J=9 Hz), 7.30 (2H, d, J=9 Hz).

(2) Preparation of 2,2-dichloro-12-(4-chlorophenyl)-11-oxododecanoic acid

The desired compound (3.90 g, yield 92.6%) was obtained as white crystalline powders in a similar method to that of Example 1 (4) from methyl 2,2-dichloro-12-(4-chlorophenyl)-11-oxododecanoate (4.36 g, 10.69 mmol).
Melting point: 56.8–57.8° C. (solvent for recrystallization: diethyl ether-n-hexane)
$^1$H-NMR (CDCl$_3$) δ: 1.18–1.40 (8H, m), 1.50–1.61 (4H, m), 2.40–2.45 (2H, m), 2.45 (2H, t, J=8 Hz), 3.67 (2H, s), 7.13 (2H, d, J=9 Hz), 7.30 (2H, d, J=9 Hz).

Example 9

(1) Preparation of methyl 2,2-dichloro-12-(4-chlorophenyl)-12-oxododecanoate

The desired compound (2.87 g, yield 93.9%) was obtained as white crystalline powders in a similar method to that of Example 6 (4) from methyl 2,2-dichloro-12-(4-chlorophenyl)-12-hydroxydodecanoate obtained in Example 3 (3) (3.07 g, 7.49 mmol).
Melting point: 55.2–56.2° C. (solvent for recrystallization: chloroform-n-hexane)
$^1$H-NMR (CDCl$_3$) δ: 1.28–1.41 (10H, m), 1.57 (2H, m), 1.72 (2H, m), 2.41 (2H, m), 2.93 (2H, t, J=8 Hz), 3.89 (3H, s), 7.43 (2H, d, J=9 Hz), 7.90 (2H, d, J=9 Hz).

(2) Preparation of 2,2-dichloro-12-(4-chlorophenyl)-12-oxododecanoic acid

The desired compound (1.74 g, yield 65.5%) was obtained as white crystalline powders in a similar method to that of Example 1 (4) from methyl 2,2-dichloro-12-(4-chlorophenyl)-12-oxododecanoate (2.75 g, 6.74 mmol).
Melting point: 82.4–83.0° C. (solvent for recrystallization: chloroform-n-hexane)
$^1$H-NMR (CDCl$_3$) δ: 1.27–1.42 (10H, m), 1.60 (2H, m), 1.72 (2H, m), 2.45 (2H, m), 2.94 (2H, t, J=8 Hz), 7.44 (2H, d, J=9 Hz), 7.91 (2H, d, J=9 Hz).

Test Example 1

The compounds of the present invention and the aforementioned Compound A and pioglitazone hydrochloride each as a reference compound were subjected to the measurements of the actions of lowering plasma glucose, insulin, and triglyceride in vivo according to the following method (Metabolism, 48, pp34–40, 1999, Journal of Medicinal Chemistry, 44, pp2601–2611, 2001).

(1) Method for the Measurement

C57BL/KsJ db/db mouse (Journal of Clinical Investigation, 85, pp 962–967, 1990) was used as an experimental animal, which was developed in The Jackson Laboratory (USA) and is known as a model animal with obesity, hyperlipemia, hyperinsulinemia, and insulin resistance.

Bloods were collected from seven weeks old db/db mice from their orbital sinus by using heparin-treated capillary tubes. After centrifugation of the bloods, plasma was collected and then subjected to measurements of concentrations of plasma glucose, insulin, and triglyceride to divide the animals. From the next day of the day of blood collection, the administrations of the compounds were started. The compounds were orally administered once a day for 14 days. On the 14th day, blood was collected from orbital sinus two hours after the administration of the compounds. Plasma was collected, and subjected to measurements of concentrations of plasma glucose, insulin, and triglyceride.

The dose required for reduction of plasma glucose concentration by 25% (ED$_{25}$) was obtained using the value of the vehicle administered group as 100% (Arznimittel-Forschung, 40, pp156–162, 1990).

(2) Results

Table 1 shows the actions of the compounds of the present invention and the reference compounds for reduction of plasma glucose, insulin, and triglyceride. The results shown in table 1 indicate that the compounds of the present invention give more potent actions for reduction of plasma glucose, insulin, and triglyceride than Compound A and pioglitazone hydrochloride.

TABLE 1

Reduction ratio of plasma glucose, insulin, and triglyceride

| Examples | Dose (mg/kg) | Reduction rate of plasma glucose | Reduction rate of plasma insulin | Reduction rate of plasma triglyceride |
|---|---|---|---|---|
| Example 2(4) | 3 | 44.4 ± 17.0 | −12.5 ± 58.1 | 53.2 ± 6.9 |
| | 10 | 66.6 ± 4.1 | 39.1 ± 21.3 | 54.1 ± 5.5 |
| | 30 | 75.2 ± 3.1 | 64.3 ± 10.1 | 55.7 ± 6.3 |
| Example 3(4) | 3 | 29.3 ± 28.7 | −2.8 ± 46.6 | 23.2 ± 24.7 |
| | 10 | 53.4 ± 14.7 | 39.0 ± 10.3 | 40.6 ± 8.9 |
| | 30 | 74.5 ± 3.0 | 61.7 ± 18.5 | 25.8 ± 24.7 |
| Example 4(4) | 3 | 35.0 ± 21.2 | −19.8 ± 71.8 | 45.5 ± 13.9 |
| | 10 | 65.2 ± 8.0 | 20.3 ± 24.9 | 58.8 ± 3.7 |
| | 30 | 67.2 ± 6.8 | 51.1 ± 20.2 | 54.1 ± 6.6 |
| Example 5(4) | 0.5 | 20.7 ± 14.3 | −22.0 ± 84.1 | 42.0 ± 17.3 |
| | 1.5 | 40.6 ± 5.8 | 39.5 ± 37.5 | 48.3 ± 6.9 |
| | 5 | 42.4 ± 11.4 | 43.8 ± 26.3 | 44.6 ± 9.7 |
| Example 5(5) | 0.5 | −10.3 ± 35.4 | 20.8 ± 32.0 | 23.0 ± 13.8 |
| | 1.5 | 28.5 ± 10.7 | 20.4 ± 38.0 | 40.5 ± 15.3 |
| | 5 | 49.2 ± 9.6 | 68.9 ± 13.2 | 37.6 ± 11.3 |
| Compound A | 1 | −5.0 ± 19.5 | 0.7 ± 77.6 | 23.4 ± 15.3 |
| | 3 | 25.4 ± 17.7 | 7.4 ± 18.7 | 27.5 ± 17.5 |
| | 10 | 65.3 ± 5.0 | 10.7 ± 61.6 | 54.6 ± 4.1 |
| Pioglitazone hydrochloride | 3 | 13.4 ± 18.3 | −24.7 ± 119.3 | 9.4 ± 15.9 |
| | 10 | 22.3 ± 22.8 | −18.7 ± 52.5 | 25.4 ± 16.9 |
| | 30 | 45.2 ± 21.2 | 13.9 ± 22.7 | 38.2 ± 8.1 |

The compounds of the present invention were found to have the actions even at lower doses. Therefore, as for the plasma glucose reducing action, doses that induce the actions were compared by calculating ED$_{25}$ values. Ratios of the effects of the compounds of the present invention and the reference compounds on reduction of plasma glucose are shown in Table 2 as ED$_{25}$ values. Among the compounds of the present invention, the compound of Example 2 (4) gave the value of 0.6 mg/kg; the compound of Example 4 (4) gave 1.1 mg/kg; and the compound of Example 5 (4) gave 0.5 mg/kg, whereas the compound A gave 2.8 mg/kg. The compounds of the present invention thus gave the same level of plasma glucose reducing action at 1/2.5 to 1/5.6 doses as that of compound A.

These results revealed that the medicine comprising the compound of the present invention was expected to achieve reduction of side effects and prevention of drug interactions when used in combination with other agents.

TABLE 2

Plasma glucose reducing action (ED$_{25}$)

| Examples | ED$_{25}$ (mg/kg) |
|---|---|
| Example 2(4) | 0.6 |
| Example 3(4) | 2.4 |
| Example 4(4) | 1.1 |
| Example 5(4) | 0.5 |
| Example 5(5) | 1.7 |
| Compound A | 2.8 |
| Pioglitazone hydrochloride | 8.3 |

INDUSTRIAL APPLICABILITY

The compound represented by the aforementioned general formula (1), a salt thereof, or an ester thereof has potent reducing actions of blood glucose, plasma insulin, and triglyceride, and is useful as an active ingredient of a medicine that enables preventive and/or therapeutic treatment of diseases such as diabetes, complications of diabetes, hyperlipemia, and atherosclerosis, without causing weight gain or obesity.

What is claimed is:

1. A compound selected from 2,2 dichloro-12-(4-chlorophenyl)-10-hydroxydodecanoic acid and 2,2 dichloro-12-(4-chlorophenyl)-11-hydroxydodecanoic acid, a salt thereof or an ester thereof.

2. A medicine which comprises as an active ingredient a substance selected from 2,2 dichloro-12-(4-chlorophenyl)-10-hydroxydodecanoic acid and 2,2 dichloro-12-(4-chlorophenyl)-11-hydroxydodecanoic acid, a salt thereof or an ester thereof.

3. The medicine according to claim 2 for therapeutic treatment of a disease selected from hyperlipemia, atherosclerosis, diabetes, complications of diabetes, inflammation, and cardiopathy.

4. The medicine according to claim 2 in a form of a pharmaceutical composition which further comprises a pharmaceutically acceptable carrier.

5. The medicine according to claim 3 in a form of a pharmaceutical composition which further comprises a pharmaceutically acceptable carrier.

6. A method of therapeutic treatment of a disease selected from hyperlipemia, atherosclerosis, diabetes, complications of diabetes, inflammation, and cardiopathy, which comprises administering to a mammal a therapeutically-effective amount of compound selected from 2,2 dichloro-12-(4-chlorophenyl)-10-hydroxydodecanoic acid and 2,2 dichloro-12-(4-chlorophenyl)-11-hydroxydodecanoic acid, a salt thereof or an ester thereof.

7. The method according to claim 6, wherein the compound is present in a composition.

8. The method according to claim 6, wherein the mammal is a human.

* * * * *